(12) United States Patent
Koo et al.

(10) Patent No.: US 8,048,650 B2
(45) Date of Patent: Nov. 1, 2011

(54) **MICROORGANISM OF *CORYNEBACTERIUM* GENUS HAVING ENHANCED L-LYSINE PRODUCTIVITY AND A METHOD OF PRODUCING L-LYSINE USING THE SAME**

(75) Inventors: Hyun-min Koo, Gyenoggi-do (KR); Young-lyeol Yang, Gyeonggi-do (KR); Hyo-jin Kim, Seoul (KR); Jun-ok Moon, Seoul (KR); Sang-jo Lim, Incheon (KR); Jong-soo Choi, Seoul (KR); Young-hoon Park, Gyeonggi-do (KR)

(73) Assignee: CJ Cheiljedang Corporation, Seoul (KR)

( * ) Notice: Subject to any disclaimer, the term of this patent is extended or adjusted under 35 U.S.C. 154(b) by 108 days.

(21) Appl. No.: 12/518,578

(22) PCT Filed: Dec. 28, 2007

(86) PCT No.: PCT/KR2007/006936
§ 371 (c)(1),
(2), (4) Date: Jun. 10, 2009

(87) PCT Pub. No.: WO2008/082181
PCT Pub. Date: Jul. 10, 2008

(65) Prior Publication Data
US 2010/0028957 A1 Feb. 4, 2010

(30) Foreign Application Priority Data
Dec. 29, 2006 (KR) .................. 10-2006-0137652

(51) Int. Cl.
*C12P 13/08* (2006.01)
*C12P 13/04* (2006.01)
*C12N 1/20* (2006.01)
*C12N 15/74* (2006.01)
*C12N 15/00* (2006.01)

(52) U.S. Cl. ................ 435/115; 435/106; 435/252.32; 435/252.3; 435/471; 435/320.1

(58) Field of Classification Search ............... 435/115, 435/106, 252.32, 252.3, 471, 320.1
See application file for complete search history.

(56) References Cited

U.S. PATENT DOCUMENTS

| | | |
|---|---|---|
| 6,221,636 B1 | 4/2001 | Hayakawa et al. |
| 6,746,855 B2 | 6/2004 | Kreutzer et al. |
| 6,872,553 B2 | 3/2005 | Eikmanns et al. |
| 6,913,909 B2 | 7/2005 | Ziegler et al. |
| 6,962,989 B1 | 11/2005 | Pompejus et al. |
| 7,160,711 B2 | 1/2007 | Bathe et al. |
| 2002/0192674 A1 | 12/2002 | Hermann et al. |
| 2002/0197605 A1 | 12/2002 | Nakagawa et al. |
| 2005/0153402 A1 | 7/2005 | Pompejus et al. |
| 2008/0293100 A1 | 11/2008 | Wendisch et al. |
| 2010/0015673 A1 | 1/2010 | Koo et al. |
| 2010/0129884 A1 | 5/2010 | Cho et al. |
| 2010/0330624 A1 | 12/2010 | Jang et al. |

FOREIGN PATENT DOCUMENTS

| | | |
|---|---|---|
| DE | 101 10 760 A1 | 8/2001 |
| JP | H07-121228 | 5/1995 |
| JP | HEI 7-121228 | 12/1995 |
| KR | 1020050065712 | 6/2005 |
| KR | 10-2008-025355 A | 3/2008 |
| WO | WO 02/053707 | 7/2002 |
| WO | WO 2005/121349 | 12/2005 |
| WO | WO 2007/039532 | 4/2007 |

OTHER PUBLICATIONS

Tzvetkov et al. (Jul. 2003) Microbiology 149(7):1659-1673, "Genetic dissection of trehalose biosynthesis in *Corynebacterium glutamicum*: Inactivation of trehalose production leads to impaired growth and altered cell wall lipid composition".
European Search Report issued Dec. 30, 2009 in PCT/KR2007/006935.
EP Search Report issued Feb. 18, 2010 in EP application serial No. 07851817.2.
Database UnitProt [Online] Jul. 5, 2004, "SubName: Full=Putative uncharacterized protein".
Ikeda and Nakagawa (Aug. 2003) Appl Microbiol Biotechnol 62:99-109, "The *Corynebacterium glutamicum* genome: features and impacts on biotechnological processes".
Mitsuhashi et al. (Nov. 2006) Biosci. Biotechnol. Biochem. 70(11):2803-2806, "Disruption of Malate:Quinone Oxidoreductase Increases L-Lysine Production by *Corynebacterium glutamicum*".
Eggeling (1994) Amino Acids 6:261-272, "Biology of L-lysine over-production by *Corynebacterium glutamicum*".
International Written Opinion dated Jan. 24, 2008 from PCT/KR2007/006936.
International Search Report dated Jan. 24, 2008 from PCT/KR2007/006936.
International Written Opinion dated Jan. 24, 2008 from PCT/KR2007/006935.
International Search Report dated Jan. 24, 2008 from PCT/KR2007/006935.
U.S. Appl. No. 12/867,649, filed Aug. 13, 2010, Jang et al.
Hayes, Finbarr (2003) Annu. Rev. Genet. 37:3-29, "Transposon-Based Strategies for Microbial Functional Genomics and Proteomics".
Mormann (Aug. 10, 2006) BMC Genomics, 7:205, doi:10.1186/1471-2164-205, "Random mutagenesis in *Corynebacterium glutamicum* ATCC 13032 using an IS6100-based transposon vector identified the last unknown gene in the histidine biosynthesis pathway".
Peters-Wendisch et al. (Nov. 2005) Applied and Environmental Microbiology, 71(11):7139-7144, "Metabolic Engineering of *Corynebacterium glutamicum* for L-Serine Production".
Tsuge et al. (2005) Microbiology 151:501-508, "A New Insertion Sequence, IS14999, from *Corynebacterium glutamicum*".
Office Action issued Jan. 7, 2011 in U.S. Appl. No. 12/518,572.

*Primary Examiner* — Ganapathirama Raghu
(74) *Attorney, Agent, or Firm* — Swanson & Bratschun, L.L.C.

(57) ABSTRACT

The present invention relates to a microorganism of *Corynebacterium* genus having enhanced L-lysine productivity and a method of producing L-lysine using the same. More particularly, the present invention relates to a recombinant microorganism of *Corynebacterium* genus having enhanced L-lysine productivity by inactivating endogenous NCgl 1090 gene having the amino acid sequence containing repeated aspartate residues and a method of producing L-lysine using the same.

6 Claims, 1 Drawing Sheet

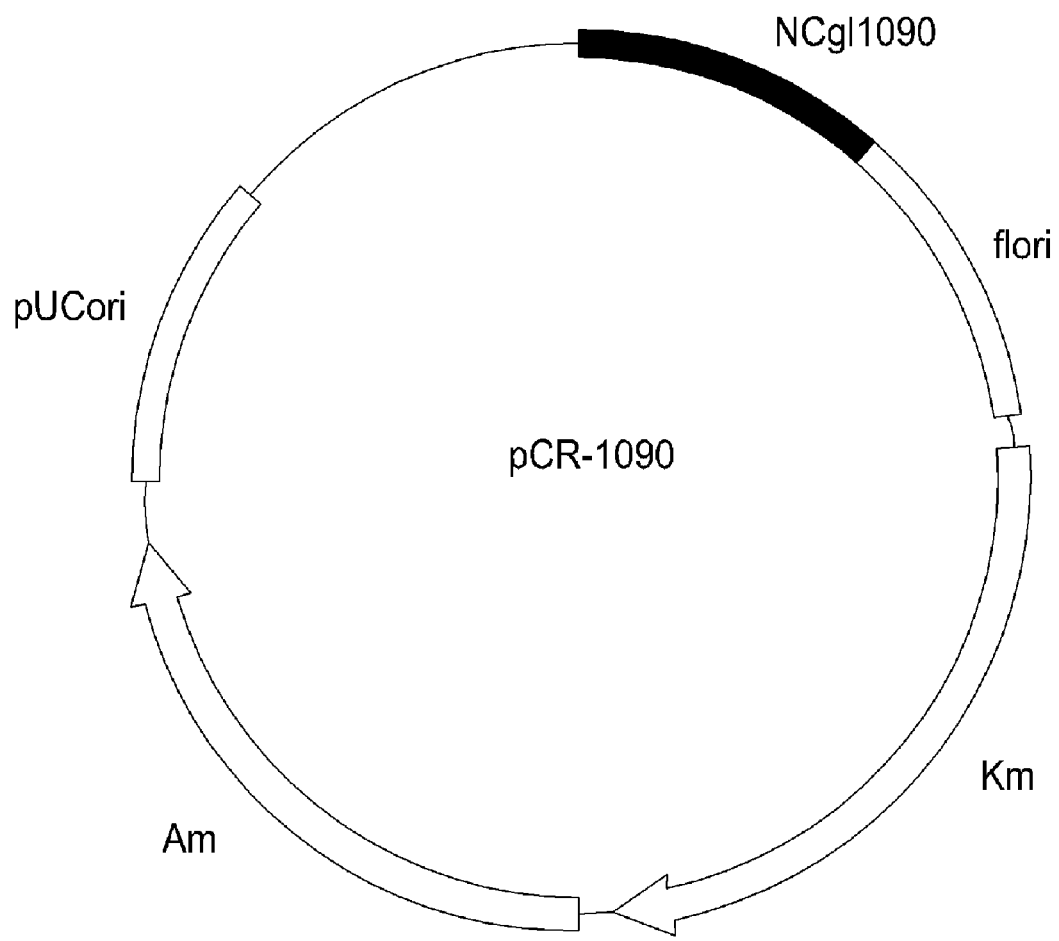
[Fig. 1]

MICROORGANISM OF *CORYNEBACTERIUM* GENUS HAVING ENHANCED L-LYSINE PRODUCTIVITY AND A METHOD OF PRODUCING L-LYSINE USING THE SAME

TECHNICAL FIELD

The present invention relates to a microorganism of *Corynebacterium* genus having enhanced L-lysine productivity and a method of producing L-lysine using the same. More particularly, the present invention relates to a recombinant microorganism of *Corynebacterium* genus having enhanced L-lysine productivity by inactivating endogenous NCgl1090 gene having the amino acid sequence containing repeated aspartate residues and a method of producing L-lysine using the same.

BACKGROUND ART

L-amino acid, in particular L-lysine has been widely used as for animal feeds, as a raw material for medicines and in pharmaceutical industry, and produced by fermentation of the microorganisms of *Corynebacterium* genus.

Microorganisms of *Corynebacterium* genus, particularly *Corynebacterium glutamicum* is a Gram-positive microorganism that are widely used in L-amino acid production. The method of producing L-amino acids using the microorganisms of *Corynebacterium* genus is very important. So, there have been many attempts made to improve the method.

One of the attempts is to improve the microorganisms of *Corynebacterium* genus that produces L-amino acid by disrupting specific genes or attenuation expressing specific genes using a recombinant DNA techniques. For example, U.S. Pat. No. 6,872,553 discloses a method of producing L-lysine of microorganisms of *Corynebacterium* genus by fermentation which comprises the following steps: a) growing microorganisms of *Corynebacterium* genus having an attenuated DNA encoding phosphoenolpyruvate (PEP) carboxykinase (PCK) by one of the mutation method selected from the group consisting of insertion or one or more base pairs in the DNA, deletion of one or more base pairs in the DNA, transition or transversion of base pairs by introducing a nonsense codon in the DNA or having reduced phosphoenolpyruvate (PEP) carboxykinase (PCK) compared with microorganisms of *Corynebacterium* genus that are not attenuated; b) concentrating desired L-amino acid product in medium or cells; and c) separating L-amino acid.

In addition, many studies on how each gene involved in L-amino acids biosynthesis affects L-amino acid production by amplifying the genes to develop microorganisms of *Corynebacterium* genus have been conducted (Eggeling, Amino Acids 6, 261-272 (1994)). Also, microorganisms of *Corynebacterium* genus can be developed by introducing foreign genes from other bacteria. For example, Japanese Laid-off Patent Publication No. Hei 7-121228 discloses a method of producing L-glutamic acid and L-proline by culturing the microorganism of *Corynebacterium* genus or *Brevibacterium* genus that contain recombinant construct between DNA fragment having genetic information involving synthesis of citric acid synthase and vector DNA, and producing L-glutamic acid and L-proline from the cultures.

However, it is still required to produce a strain with enhanced L-lysine productivity, in spite of the above trials.

DISCLOSURE OF INVENTION

Technical Problem

The present inventors have studied to develop a microorganism capable of producing L-lysine with high yield with targeting endogenous NCgl1090 gene having repeated aspartate residues in its amino acid sequence in microorganism of *Corynebacterium* genus. And the present inventors tried to increase L-lysine productivity with reducing unnecessary intracellular consumption of aspartate, the intermediate of lysine biosynthesis pathway, by inactivating the target gene above.

It is an object of the present invention to provide a microorganism of *Corynebacterium* genus with enhanced L-lysine productivity.

It is another object of the present invention to provide a method of producing L-lysine using the microorganism above.

Technical Solution

The above objects and other objects of the present invention can be achieved by the following embodiments of the present invention.

The present invention is described in detail hereinafter.

To achieve the above objects, the present invention provides a microorganism having L-lysine productivity, more preferably a microorganism of *Corynebacterium* genus with enhanced L-lysine productivity by inactivating endogenous NCgl1090 gene therein.

In this invention, the microorganism having L-lysine productivity can be selected from the group consisting of *Corynebacterium glutamicum* ATCC 13032, *Corynebacterium thermoaminogenes* FERM BP-1539, *Corynebacterium glutamicum* KFCC 10881, and *Corynebacterium glutamicum* KFCC 11001, but not always limited thereto.

Aspartate is an intermediate of lysine biosynthesis pathway, which is functioning as a unit of cell composition or protein synthesis or a regulator. As a unit of cell composition, aspartate is used for the synthesis of nucleic acid, amino aid or fat. As a unit of protein synthesis, aspartate is used for protein structure or as a major functional group. In particular, as for the unit of protein synthesis, genes translated into proteins are divided into two groups; one is the genes essential for the cell growth, maintenance, and regulation and the other is the genes non-essential for those processes. The non-essential genes are divided as follows; genes not required anymore according to the other genes having equal functions; foreign genes introduced from out side such as virus genes; genes necessary for some cases but not necessary for other conditions such as for the production of lysine; and genes whose functions have not been explained, yet.

Cells consume aspartate massively to compose proteins of the non-essential genes. Therefore, if the non-essential genes are eliminated, it is considered that massive amount of aspartate consumption for the non-essential genes can be reduced, which favors the reduction of unnecessary aspartate consumption and also favors the production of lysine under the same condition.

To develop a microorganism with improved L-lysine productivity, the present inventors searched a gene that contains aspartate residues, the intermediate of lysine biosynthesis, in its amino acid sequence encoding a protein, more than any other genes, from the genome sequence database of completely analyzed sequence of *Corynebacterium glutamicum* ATCC 13032 (NCBI GI: 19552361, SEQ. ID. NO: 1). As a result, it is confirmed that the repeated aspartate residues were presented in C-terminal of NCgl1090 protein having the amino acid sequence represented by SEQ. ID. NO: 3. However, how those repeated aspartate residues on the amino acid sequence could be involved in lysine biosynthesis in a lysine producing strain has not been explained.

In this invention, NCgl1090 gene is a gene that endogenously exists in the microorganism of *Corynebacterium* genus, and is known as a gene encoding a hypothetical protein whose functions are unknown. The activity of the gene is predicted from a complete sequence analysis of a genome of *Corynebacterium glutamicum* ATCC 13032 and confirmed to have repeated aspartate residues at C-terminal and preferably had the nucleotide sequence represented by SEQ. ID. NO: 1. The endogenous NCgl1090 gene of a microorganism of *Corynebacterium* genus of the present invention preferably has high homology with the sequence represented by SEQ. ID. NO: 1.

In this invention, the "inactivation" can be induced by any inactivation method known to those in the art. The term "inactivation" herein intends to mean that the expression of the NCgl1090 gene is reduced to a low level compared to a wild type strain, or genes that are not expressed and genes that express products having no activity or reduced activity in spite of being expressed are produced.

In this invention, the "inactivation" can be induced by one or more mutation methods selected from the group consisting of insertion of one or more base pairs in NCgl1090 gene, deletion of one or more base pairs in the gene, transition or transversion of base pairs by inserting nonsense codon in the gene.

In a preferred embodiment of the present invention, the microorganism containing the inactivated endogenous NCgl1090 gene can be obtained by culturing a microorganism of *Corynebacterium* genus transformed with the vector containing a part of the NCgl1090 gene and an antibiotic marker in the presence of antibiotics. Preferably, the vector is a pCR-1090 vector containing the NCgl1090 gene fragment of SEQ. ID. NO: 2. The microorganism is transformed with the vector containing a part of the gene sequence, followed by culture in the presence of a selection marker. Then, homologous recombination occurs between a part of the gene and the endogenous gene of the microorganism. By the homologous recombination, the endogenous genes of the microorganism are recombinated and the recombinant gene that contains the marker is only selected by the selection marker. As a result, the microorganism of *Corynebacterium* genus of which endogenous NCgl1090 gene is inactivated can be obtained. However, a method for preparing the microorganism of *Corynebacterium* genus according to the present invention is not limited to the homologous recombination, and any method known to those in the art can be used.

The transformed microorganism with improved L-lysine productivity of the present invention may be *Corynebacterium glutamicum* KFCC10881-CO01-0018 (Accession No: KCCM 10810P).

The present invention also provides a method of producing L-lysine using the transformed microorganism. More particularly, the present invention provides a method of producing L-lysine comprising the steps of producing L-lysine in the cultures or cells by culture of the microorganism of *Corynebacterium* genus; and collecting L-lysine from the cultures.

In the method of the present invention, the culture of microorganism of *Corynebacterium* genus can be performed by any culture method and culture conditions known to those in the art.

The medium for the culture of the microorganism of *Corynebacterium* genus can be selected from those described in Manual of Methods for General Bacteriology by the American Society for Bacteriology (Washington D.C., USA, 1981).

The medium includes various carbon sources, nitrogen sources and trace elements. The carbon source is exemplified by sugar and carbohydrate such as glucose, sucrose, lactose, fructose, maltose, starch, cellulose; oil and fat such as soybean oil, sunflower oil, castor oil and coconut oil; fatty acid such as palmitic acid, stearic acid, and linoleic acid; alcohol such as glycerol and ethanol; and organic acid such as acetic aid. One of these compounds or a mixture thereof can be used as a carbon source.

The nitrogen source is exemplified by such organic nitrogen source as peptone, yeast extract, gravy, malt extract, corn steep liquor (CSL) and bean flour and such inorganic nitrogen source as urea, ammonium sulfate, ammonium chloride, ammonium phosphate, ammonium carbonate and ammonium nitrate. One of these compounds or a mixture thereof can be used as a nitrogen source.

The medium herein can additionally include potassium dihydrogen phosphate, dipotassium hydrogen phosphate and corresponding sodium-containing salts as a phosphate source. The medium can also include a metal salt such as magnesium sulfate or iron sulfate. In addition, amino acids, vitamins and proper precursors can be added as well. The medium or the precursor can be added to the culture by batch-type or continuously.

The pH of the culture can be controlled using a basic compound such as sodium hydroxide, potassium hydroxide or ammonia, or an acid compound such as phosphoric acid or sulfuric acid during the cultivation. The generation of air bubbles can be inhibited during the cultivation by using an antifoaming agent such as fatty acid polyglycol ester. To maintain aerobic condition of the culture, oxygen or oxygen-containing gas (ex, air) can be injected into the culture. The temperature of the culture is preferably 20-45° C., more preferably 25-40° C. The cultivation can be continued until the production of L-amino acid reaches a wanted level, and the preferable culture time is 10-160 hours.

In this method, the culture can be performed by continuous or batch type method such as batch, fed-batch and repeated fed-batch cultures. It is well understood by those in the art that the culture method can be selected appropriately.

L-amino acid may be separated and analyzed by anion exchange chromatography and following ninhydrin derivatization.

In addition to the identification of the gene, the present inventors further inactivated NCgl1090 gene, the endogenous gene of the microorganism of *Corynebacterium* genus, to measure the lysine productivity. And as a result, it was confirmed that the lysine productivity was increased.

BRIEF DESCRIPTION OF THE DRAWINGS

The application of the preferred embodiments of the present invention is best understood with reference to the accompanying drawings, wherein:

FIG. 1 is a diagram showing the pCR-1090 vector wherein 401 bp NCgl1090 gene fragment was cloned.

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

In the following examples, to confirm the effect of NCgl1090 having repeated aspartate residues in its amino acid sequence on the production of lysine, NCgl1090, the endogenous gene of *Corynebacterium glutamicum* KFCC10881, was inactivated. And the strain containing the inactivated NCgl1090 was cultured and the lysine productivity was measured.

Example 1

Construction of a Vector for Inactivating NCgl1090 Gene, the Endogenous Gene of the Microorganism of *Corynebacterium* Genus In this example, 401 bp fragment of the NCgl1090 gene (SEQ. ID. NO: 2) ($160^{st}$-$560^{th}$ nucleotides of the sequence represented by SEQ. ID. NO: 1) was amplified by PCR using chromosomal DNA of *Corynebacterium glutamicum* (ATCC 13032) as a template with oligonucleotide primers represented by SEQ. ID. NO: 4 and NO: 5 to construct NCgl1090 gene disruption vector containing a part of the endogenous NCgl1090 gene and an antibiotic marker. PCR was performed as follows; denaturation at 96° C. for 30 seconds, annealing at 52° C. for 30 seconds and polymerization at 72° C. for 30 seconds (30 cycles). The amplified NCgl1090 gene fragment was cloned into *E. coli* plasmid pCR.2.1 by using TOPO cloning kit (Invitrogen, USA). As a result, pCR-1090 vector was constructed. FIG. 1 is a diagram showing the pCR-1090 vector that 500 bp NCgl1090 gene fragment was cloned.

Example 2

Construction of a Microorganism Producing L-Lysine having Inactivated NCgl1090 Gene, the Endogenous Gene of *Corynebacterium glutamicum* KFCC10881

*Corynebacterium glutamicum* KFCC10881, an microorganism producing L-lysine, was transformed with the pCR-1090 vector constructed in example 1 by electric pulse method according to the method described in Appl. Microbiol. Biotechnol., (1999) 52:541-545. PCR was performed on the 2nd day of culture to confirm the disruption of the NCgl1090 gene in the transformed microorganism. Particularly, PCR was performed using chromosomal DNA of the transformed microorganism as a template with oligonucleotide primers represented by SEQ. ID. NO: 6 and NO: 7. As a result, approximately 5030 bp ($1^{st}$-$804^{th}$ nucleotides of the sequence represented by SEQ. ID. NO: 1) NCgl1090 gene fragment containing pCR-1090 plasmid was amplified. From the PCR, it was confirmed that the NCgl1090 gene was disrupted by insertion of pCR-1090 plasmid into the middle of the endogenous NCgl1090 gene on chromosomal DNA by cross-over through homologous recombination.

The obtained microorganism was named "*Corynebacterium glutamicum* KFCC10881-CO01-0018", which was deposited at KCCM (Korean Culture Center of Microorganisms) of KFCC (Korean Federation of Culture Collection), the International Depository Authority located at 361-221, Hongje-1-Dong, Seodaemungu-Gu, Seoul, Korea, on Dec. 7, 2006 (Accession No: KCCM 10810P).

Example 3

Production of Lysine by Using *Corynebacterium glutamicum* KFCC10881-CO01-0018

The transformant *Corynebacterium glutamicum* KFCC10881-CO01-0018 (KCCM 10810P) prepared in example 2, was cultured to produce L-lysine.

First, the *Corynebacterium glutamicum* mother strain KFCC10881 and the transformed KFCC10881-CO01-0018 (KCCM 10810P) were inoculated in a 250 ml corner-baffled flask containing 25 ml of the seed culture having the following composition, followed by culture at 30° C. for 20 hours with stirring at 200 rpm. 1 mL of the seed culture was inoculated in a 250 ml corner-baffled flask containing 24 ml of the production medium having the following composition, followed by culture at 30° C. for 120 hours with stirring at 200 rpm. Upon completion of the culture, L-lysine production was measured by HPLC (Waters 2457).

As a result, the *Corynebacterium glutamicum* mother strain KFCC10881 and the *Corynebacterium glutamicum* KFCC10881-CO01-0018 (KCCM 10810P) produced 45 g/l and 50 g/l of L-lysine in their culture media respectively as hydrochloride of L-lysine.

Seed Medium (pH 7.0):

Raw sugar 20 g, Peptone 10 g, Yeast extract 5 g, Urea 1.5 g, $KH_2PO_4$ 4 g, $K_2HPO_4$ 8 g, $MgSO_4 7H_2O$ 0.5 g, Biotin 100□, Thiamine HCl 1000□, Calcium-pantothenic acid 2000□, nicotinamide 2000□ (in 1 liter of process water)

Production Medium (pH 7.0):

Raw sugar 100 g, $(NH_4)_2SO_4$ 40 g, Soybean protein 2.5 g, Corn Steep Solids 5 g, Urea 3 g, $KH_2PO_4$ 1 g, $MgSO_4 7H_2O$ 0.5 g, Biotin 100□, Thiamine HCl 1000□, Calcium-pantothenic acid 2000□, Nicotinamide 3000□, $CaC_3O$ 30 g (in 1 liter of process water)

Example 4

Collection of L-Lysine from the *Corynebacterium glutamicum* KFCC 10881-CO01-0018 Culture

*Corynebacterium glutamicum* KFCC10881-CO01-0018 was cultured in the medium containing molasses and raw sugar. pH of 1 L of the obtained lysine culture was adjusted to 2.0 using HCl and then Ca ions were changed into the form of $CaSO_4$ or $CaCl_2$. The culture medium was spilled on the cation exchange resin revived as ammonium ions (Diaion SK-L10) upwardly, followed by adsorption. The cells remaining in the resin layer were eliminated by washing with desalted water, followed by elution using 2 N ammonium hydroxide. As a result, lysine was collected at high concentration. The collected solution containing lysine was concentrated and pH of the solution was regulated as 5.0 by HCl, followed by cooling crystallization at 20° C. After crystallization, the obtained slurry was centrifuged to give the primary wet product. The mother solution was concentrated by batch-type, followed by crystallization to obtain the secondary wet product. The primary and the secondary wet products were mixed and dried to give 47.5 g of dried lysine product (lysine content: 98.5%).

INDUSTRIAL APPLICABILITY

As explained hereinbefore, according to the present invention, L-lysine productivity can be increased by inactivating NCgl1090 gene, the endogenous gene of *Corynebacterium glutamicum* KFCC10881-CO01-0018 (KCCM 10810P). The method of the present invention facilitates the production of L-lysine at high concentration, resulting in the increase of L-lysine productivity.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An isolated *Corynebacterium glutamicum* microorganism having enhanced L-lysine productivity by inactivating the endogenous NCgl1090 gene having the nucleotide sequence of SEQ. ID. NO:1 with repeated aspartate residues in its amino acid sequence, wherein said inactivation is induced by one or more mutation methods selected from the group consisting of insertion of one or more base pairs in the gene, deletion of one or more base pairs in the gene, transition or transversion of base pairs by inserting nonsense codon in the gene.

2. The *Corynebacterium glutamicum* according to claim 1, wherein said inactivation is induced by transformation of the *Corynebacterium glutamicum* with a vector comprising a part of the endogenous NCgl1090 gene and an antibiotic marker.

3. The *Corynebacterium glutamicum* according to claim 2 is *Corynebacterium glutamicum* KFCC 10881-CO01-0018 (KCCM 10810P) selected by culture in the presence of antibiotics.

4. A method of producing L-lysine comprising the steps of:
producing L-lysine in cultures or cells by culture of an isolated *Corynebacterium glutamicum* microorganism having enhanced L-lysine productivity by inactivating the endogenous NCgl1090 gene having the nucleotide sequence of SEQ. ID. NO:1 with repeated aspartate residues in its amino acid sequence, wherein the said inactivation is induced by one or more mutation methods selected from the group consisting of insertion of one or more base pairs in the gene, deletion of one or more base pairs in the gene, transition or transversion of base pairs by inserting nonsense codon in the gene;
and
collecting L-lysine from the cultures.

5. The method according to claim 4, wherein said inactivation is induced by transformation of the *Corynebacterium glutamicum* with a vector comprising part of the endogenous NCgl1090 gene and an antibiotic marker.

6. The method according to claim 5, wherein the *Corynebacterium glutamicum* is *Corynebacterium glutamicum* KFCC 10881-CO01-0018 (KCCM 10810P) selected by culture in the presence of antibiotics.

* * * * *

UNITED STATES PATENT AND TRADEMARK OFFICE
CERTIFICATE OF CORRECTION

PATENT NO. : 8,048,650 B2
APPLICATION NO. : 12/518578
DATED : November 1, 2011
INVENTOR(S) : Hyun-min Koo et al.

It is certified that error appears in the above-identified patent and that said Letters Patent is hereby corrected as shown below:

In the Specification

Column 3, Line 24, change "by inserting" to --for inserting--;

In the Claims

Column 11, Claim 1, Line 25, change "by inserting" to --for inserting--;

Column 12, Claim 4, Line 24, change "by inserting" to --for inserting--.

Signed and Sealed this
Twenty-first Day of February, 2023

Katherine Kelly Vidal
*Director of the United States Patent and Trademark Office*

SEQUENCE LISTING

<160> NUMBER OF SEQ ID NOS: 7

<210> SEQ ID NO 1
<211> LENGTH: 804
<212> TYPE: DNA
<213> ORGANISM: Corynebacterium glutamicum

<400> SEQUENCE: 1

```
atgagctttt ttgaggacat cgcggctgga cttgatagtg acggtatcga gtcccgcgta      60
aacggcgaca caatgttcgt tccgatcacc tctgacttgg aaatccagtt cgtggagatc     120
gattccctcc tacctgcagc aaacgtttat atcgctgcag ccaatgttga tgaagacgat     180
gatgagttcg aggcagttct cgtttcggtg gtgttctctg ttgaggatgc tgtcgctgct     240
gtcgcaaagc atgttgctac tgatcaggtg gtgactgtgc tgcgtgatct acttgaagga     300
actgatgaac gcatccagga tttggagttt ttccaggatg cagtgaatgc aaatttggtt     360
cgtgcggaag tcggccagaa ttctgagctt caggttttgg tcgaggttga agacggcgtc     420
ccaaccgcaa cggtcaattt catcgcgatc ggtgagtcct ttgaagatct gattgatcag     480
gccattgaag aattgtggga atccgacggc gacgcagttc tatcggatga agatcgccaa     540
cgcatgttcg ctgatttgac ctccgagttg aatttgtca ctgatgaagt cctcgacttg      600
ggtaccttca ctgattttga tgacttttc gatatccttt ccctcgccga tgaccaggct     660
gaggattggg aagcacagct cgttcctttt gaggacgagg aatttgatga gccggatgtt     720
tatgaccttt tcgtcgatga ctctgaagaa gatgacgacg acctcgatga tgacgaggac     780
gatgaggatg atgacgaaga ctag                                            804
```

<210> SEQ ID NO 2
<211> LENGTH: 401
<212> TYPE: DNA
<213> ORGANISM: Corynebacterium glutamicum

<400> SEQUENCE: 2

```
gccaatgttg atgaagacga tgatgagttc gaggcagttc tcgtttcggt ggtgttctct      60
gttgaggatg ctgtcgctgc tgtcgcaaag catgttgcta ctgatcaggt ggtgactgtg     120
ctgcgtgatc tacttgaagg aactgatgaa cgcatccagg atttggagtt tttccaggat     180
gcagtgaatg caaatttggt tcgtgcggaa gtcggccaga attctgagct tcaggttttg     240
gtcgaggttg aagacggcgt cccaaccgca acggtcaatt tcatcgcgat cggtgagtcc     300
tttgaagatc tgattgatca ggccattgaa gaattgtggg aatccgacgg cgacgcagtt     360
ctatcggatg aagatcgcca acgcatgttc gctgatttga c                          401
```

<210> SEQ ID NO 3
<211> LENGTH: 267
<212> TYPE: PRT
<213> ORGANISM: Artificial Sequence
<220> FEATURE:
<223> OTHER INFORMATION: NCgl1090 amino acid sequences encoding a
      hypothetical protein

<400> SEQUENCE: 3

```
Met Ser Phe Phe Glu Asp Ile Ala Ala Gly Leu Asp Ser Asp Gly Ile
 1               5                  10                  15

Glu Ser Arg Val Asn Gly Asp Thr Met Phe Val Pro Ile Thr Ser Asp
            20                  25                  30

Leu Glu Ile Gln Phe Val Glu Ile Asp Ser Leu Leu Pro Ala Ala Asn
```

35                  40                  45
Val Tyr Ile Ala Ala Asn Val Asp Glu Asp Asp Glu Phe Glu
         50                  55                  60

Ala Val Leu Val Ser Val Val Phe Ser Val Glu Asp Ala Val Ala Ala
 65                  70                  75                  80

Val Ala Lys His Val Ala Thr Asp Gln Val Val Thr Val Leu Arg Asp
                     85                  90                  95

Leu Leu Glu Gly Thr Asp Glu Arg Ile Gln Asp Leu Glu Phe Phe Gln
                100                 105                 110

Asp Ala Val Asn Ala Asn Leu Val Arg Ala Glu Val Gly Gln Asn Ser
            115                 120                 125

Glu Leu Gln Val Leu Val Glu Val Asp Gly Val Pro Thr Ala Thr
130                 135                 140

Val Asn Phe Ile Ala Ile Gly Glu Ser Phe Glu Asp Leu Ile Asp Gln
145                 150                 155                 160

Ala Ile Glu Glu Leu Trp Glu Ser Asp Gly Asp Ala Val Leu Ser Asp
                165                 170                 175

Glu Asp Arg Gln Arg Met Phe Ala Asp Leu Thr Ser Glu Leu Glu Phe
            180                 185                 190

Val Thr Asp Glu Val Leu Asp Leu Gly Thr Phe Thr Asp Phe Asp Arg
        195                 200                 205

Leu Phe Asp Ile Leu Ser Leu Ala Asp Gln Ala Glu Asp Trp Glu
    210                 215                 220

Ala Gln Leu Val Pro Phe Glu Asp Glu Phe Asp Glu Pro Asp Val
225                 230                 235                 240

Tyr Asp Leu Phe Val Asp Asp Ser Glu Glu Asp Asp Asp Leu Asp
                245                 250                 255

Asp Asp Glu Asp Asp Glu Asp Asp Glu Asp
            260                 265

<210> SEQ ID NO 4
<211> LENGTH: 20
<212> TYPE: DNA
<213> ORGANISM: Artificial Sequence
<220> FEATURE:
<223> OTHER INFORMATION: primer 1 for amplifying a partial region
      (160-560nt) of NCgl1090

<400> SEQUENCE: 4
gccaatgttg atgaagacga                                              20

<210> SEQ ID NO 5
<211> LENGTH: 20
<212> TYPE: DNA
<213> ORGANISM: Artificial Sequence
<220> FEATURE:
<223> OTHER INFORMATION: primer 2 for amplifying a partial region
      (160-560nt) of NCgl1090

<400> SEQUENCE: 5
gtcaaatcag cgaacatgcg                                              20

<210> SEQ ID NO 6
<211> LENGTH: 20
<212> TYPE: DNA
<213> ORGANISM: Artificial Sequence
<220> FEATURE:
<223> OTHER INFORMATION: primer 3 for amplifying NCgl1090 entire gene

<400> SEQUENCE: 6

```
atgagctttt ttgaggacat                                          20

<210> SEQ ID NO 7
<211> LENGTH: 20
<212> TYPE: DNA
<213> ORGANISM: Artificial Sequence
<220> FEATURE:
<223> OTHER INFORMATION: primer 4 for amplifying NCgl1090 entire gene

<400> SEQUENCE: 7
ctagtcttcg tcatcatcct                                          20
```